United States Patent
Elmaanaoui et al.

(10) Patent No.: US 10,806,329 B2
(45) Date of Patent: Oct. 20, 2020

(54) OPTICAL PROBES WITH OPTICAL-CORRECTION COMPONENTS

(71) Applicant: Canon U.S.A., Inc., Melville, NY (US)

(72) Inventors: Badr Elmaanaoui, Belmont, MA (US); Tzu-Yu Wu, Malden, MA (US)

(73) Assignee: Canon U.S.A., Inc., Melville, NY (US)

( * ) Notice: Subject to any disclaimer, the term of this patent is extended or adjusted under 35 U.S.C. 154(b) by 225 days.

(21) Appl. No.: 15/879,340

(22) Filed: Jan. 24, 2018

(65) Prior Publication Data
US 2019/0223700 A1 Jul. 25, 2019

(51) Int. Cl.
| | |
|---|---|
| *A61B 1/00* | (2006.01) |
| *A61B 1/07* | (2006.01) |
| *G02B 23/24* | (2006.01) |
| *A61B 5/00* | (2006.01) |
| *G02B 13/00* | (2006.01) |

(52) U.S. Cl.
CPC ...... *A61B 1/00188* (2013.01); *A61B 1/00096* (2013.01); *A61B 1/07* (2013.01); *G02B 23/2469* (2013.01); *A61B 1/00177* (2013.01); *A61B 1/00179* (2013.01); *A61B 1/00181* (2013.01); *A61B 5/0035* (2013.01); *A61B 5/0066* (2013.01); *A61B 5/0071* (2013.01); *A61B 5/0084* (2013.01); *G02B 13/00* (2013.01); *G02B 23/243* (2013.01)

(58) Field of Classification Search
CPC .. G02B 6/32; G02B 27/0025; A61B 1/00096; A61B 1/00179; A61B 1/00188
See application file for complete search history.

(56) References Cited

U.S. PATENT DOCUMENTS

| | | | |
|---|---|---|---|
| 5,509,917 A | * | 4/1996 | Cecchetti ............... A61B 18/24 606/13 |
| 5,554,100 A | | 9/1996 | Leiner et al. |

(Continued)

FOREIGN PATENT DOCUMENTS

| | | |
|---|---|---|
| JP | H04-60608 A | 2/1992 |
| JP | H7-171162 A | 7/1995 |

(Continued)

OTHER PUBLICATIONS

Max Born, et al., Principles of Optics: Electromagnetic Theory of Propagation, Interference and Diffraction of Light, 6th ed., Pergamon Press, 1980, pp. 169-174 and 214-217 (and title and copyright pages included) (The year of publication for this reference is sufficiently earlier than the effective U.S. filing date and any foreign priority date so that the particular month of publication is not in issue.).

(Continued)

*Primary Examiner* — Daniel Petkovsek
(74) *Attorney, Agent, or Firm* — Canon U.S.A., Inc. I.P. Division

(57) ABSTRACT

Some embodiments of a device comprise a sheath, a first light-guiding component, a second light-guiding component, an optical-focusing component, and an optical-correction component. The second light-guiding component and the optical-focusing component are aligned on an optical axis. Also, the optical-correction component does not directly contact the optical-focusing component, and the optical-correction component is not positioned on the optical axis.

10 Claims, 10 Drawing Sheets

(56) References Cited

U.S. PATENT DOCUMENTS

| | | | |
|---|---|---|---|
| 6,433,937 B1 | 8/2002 | Konno | |
| 6,445,939 B1 | 9/2002 | Swanson | |
| 6,501,878 B2 | 12/2002 | Hughes | |
| 6,564,087 B1 | 5/2003 | Pitris et al. | |
| 6,620,154 B1 * | 9/2003 | Amirkhanian | A61B 18/22 606/17 |
| 6,751,379 B2 * | 6/2004 | Capewell | G02B 6/29367 385/31 |
| 6,801,375 B2 | 10/2004 | Hayashide | |
| 6,954,296 B2 | 10/2005 | Takakubo | |
| 7,366,376 B2 | 4/2008 | Shishkov | |
| 7,457,044 B2 | 11/2008 | Ohzawa | |
| 7,492,987 B2 | 2/2009 | Yeik et al. | |
| 7,680,378 B2 | 3/2010 | Alphonse | |
| 7,813,609 B2 | 10/2010 | Petersen | |
| 8,180,134 B2 | 5/2012 | Wang | |
| RE43,875 E | 12/2012 | Shishkov | |
| 8,425,500 B2 | 4/2013 | Hanley et al. | |
| 8,515,221 B2 | 8/2013 | Flanders | |
| 8,582,934 B2 * | 11/2013 | Adler | A61B 5/0066 385/33 |
| 8,641,296 B2 * | 2/2014 | Nishimura | G02B 6/425 385/31 |
| 8,781,287 B2 | 7/2014 | Flanders | |
| 8,971,679 B2 | 3/2015 | Ho | |
| RE45,512 E | 5/2015 | Tearney | |
| 9,036,966 B2 | 5/2015 | Bhagavatula | |
| 9,069,122 B2 | 6/2015 | Takeuchi | |
| 9,087,368 B2 | 7/2015 | Tearney | |
| 9,164,272 B2 | 10/2015 | Maillard | |
| 9,318,810 B2 | 4/2016 | Zelenski | |
| 9,488,782 B2 | 11/2016 | Griffin | |
| 9,662,173 B1 | 5/2017 | Griffin | |
| 10,234,676 B1 | 3/2019 | Elmaanaoui | |
| 2002/0076180 A1 | 6/2002 | Miyano | |
| 2004/0133071 A1 | 7/2004 | Alekseenko et al. | |
| 2005/0165315 A1 | 7/2005 | Zuluaga | |
| 2006/0067620 A1 | 3/2006 | Shishkov | |
| 2007/0159601 A1 | 7/2007 | Ho et al. | |
| 2007/0233396 A1 | 10/2007 | Tearney | |
| 2008/0013960 A1 | 1/2008 | Tearney | |
| 2009/0244545 A1 | 10/2009 | Toida | |
| 2009/0262361 A1 | 10/2009 | Tanioka et al. | |
| 2009/0306477 A1 | 12/2009 | Togino | |
| 2011/0137124 A1 | 6/2011 | Milner | |
| 2011/0141759 A1 | 6/2011 | Smith | |
| 2012/0101374 A1 | 4/2012 | Tearney et al. | |
| 2013/0235176 A1 | 9/2013 | Miyano | |
| 2014/0288417 A1 | 9/2014 | Schmidtlin et al. | |
| 2015/0025369 A1 | 1/2015 | Bhagavatula et al. | |
| 2015/0378105 A1 | 12/2015 | Godbout et al. | |
| 2016/0274345 A1 | 9/2016 | Ueno et al. | |
| 2016/0299170 A1 | 10/2016 | Ito et al. | |
| 2017/0168232 A1 | 6/2017 | Tearney et al. | |
| 2017/0235126 A1 | 8/2017 | DiDomenico | |
| 2018/0070932 A1 | 3/2018 | Tearney et al. | |
| 2018/0256032 A1 | 9/2018 | Takeuchi et al. | |
| 2019/0196188 A1 | 6/2019 | Hirata et al. | |
| 2019/0223699 A1 | 7/2019 | Wu | |
| 2019/0227297 A1 | 7/2019 | Wu | |
| 2019/0227298 A1 | 7/2019 | Elmaanaoui | |

FOREIGN PATENT DOCUMENTS

| | | |
|---|---|---|
| JP | 2010-533049 A | 10/2010 |
| JP | 2011-147705 A | 8/2011 |
| JP | 2012-229976 A | 11/2012 |
| JP | 2013-524930 A | 6/2013 |
| JP | 2015-532179 A | 11/2015 |
| JP | 2016-202866 A | 12/2016 |
| WO | 2014/157645 A1 | 10/2014 |
| WO | 2015116939 A1 | 8/2015 |
| WO | 2016077252 A1 | 5/2016 |

OTHER PUBLICATIONS

Eugene Hecht, Optics, 4th ed., Pearson Eduction, Adelphi University, 2002, pp. 261-264 (and title and copyright pages included) (The year of publication for this reference is sufficiently earlier than the effective U.S. filing date and any foreign priority date so that the particular month of publication is not in issue.).

Frank L. Pedrotti, et al., Introduction to Optics, 2nd ed, Prentice-Hall, Inc., Upper Saddle River, New Jersey, 1993, pp. 98-100 (and title and copyright pages included) (The year of publication for this reference is sufficiently earlier than the effective U.S. filing date and any foreign priority date so that the particular month of publication is not in issue.).

Yu-Kuan Lu et al., Asymmetric elliptic-cone-shaped microlens for efficient coupling to high-power laser diodes, Optics Express, vol. 15, No. 4, Feb. 19, 2007.

SPIE, Gradient Index Lens, Optipedia, Internet Archive Wayback Machine, May 16, 2016, downloaded from http://web.archive.org/web/20160516035942/http://spie.org/publications/tt48_55_gradient_index_lens.

Zhen Qiu et al., New Endoscopic Imaging Technology Based on MEMs Sensors and Actuators, Micromachines 2017, Jul. 2017.

Tianshi Wang et al., Numerical Analysis of Astigmatism Correction in Gradient Refractive Index Lens Based Optical Coherence Tomography Catheters, Applied Optics, 51(21):5244-5252, Jul. 20, 2012.

Woonggyu Jung et al., Numerical Analysis of Gradient Index Lens-Based Optical Coherence Tomography Imaging Probes, Journal of Biomedical Optics, vol. 15(6), Nov. 2010.

D. Yelin et al., Three-dimensional miniature endoscopy, Nature, Oct. 19, 2006, pp. 765—vol. 443.

* cited by examiner

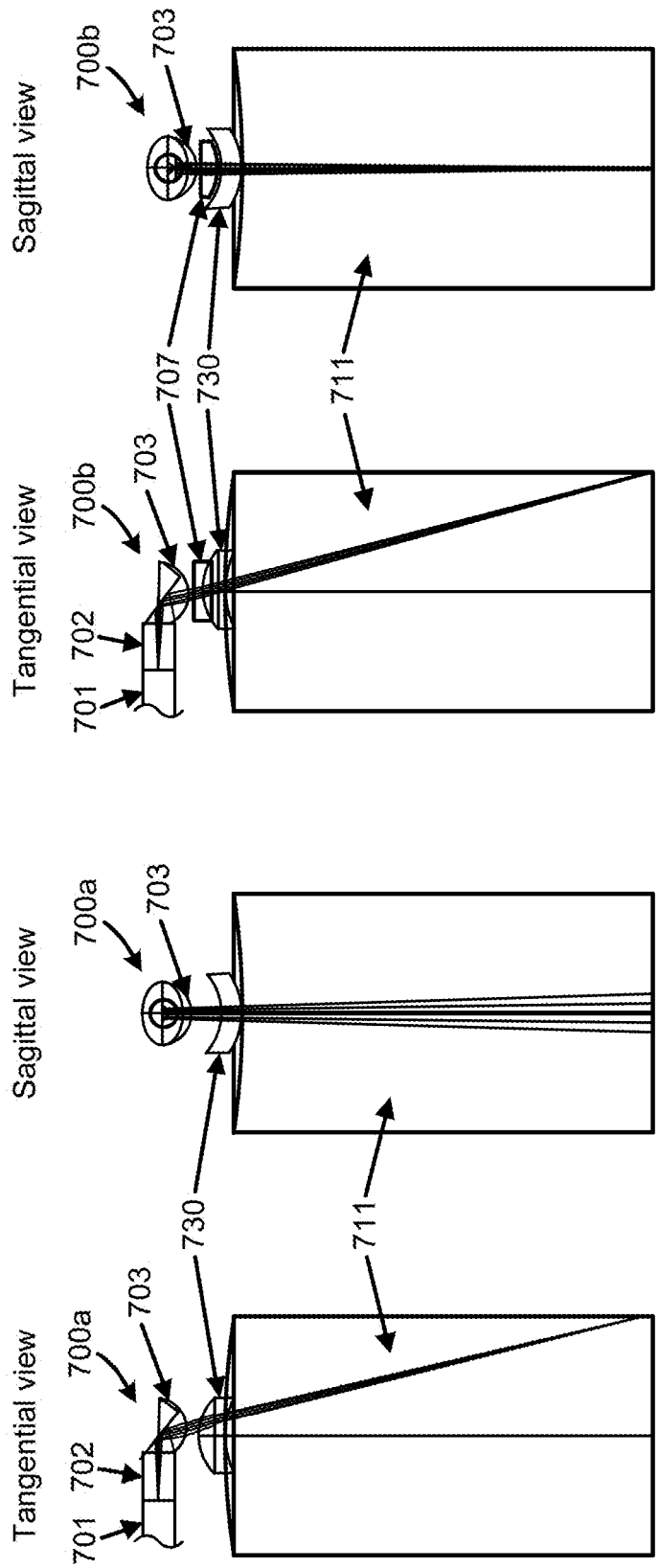

OPTICAL PROBES WITH OPTICAL-CORRECTION COMPONENTS

BACKGROUND

This application generally concerns optical probes.

An optical-imaging catheter or endoscope's optical system is usually fragile and therefore is often protected by a sheath. Astigmatism is created in the optical system by the shape of the sheath. Astigmatism causes the foci of the beams of light in two orthogonal directions to converge at different distances with different beam sizes or to diverge in one direction while converging in another direction. This astigmatism reduces the image quality of the optical system.

SUMMARY

Some embodiments of a device comprise a sheath; a first light-guiding component; a second light-guiding component; an optical-focusing component, wherein the second light-guiding component and the optical-focusing component are aligned on an optical axis; and an optical-correction component. The optical-correction component does not directly contact the optical-focusing component, and the optical-correction component is not positioned on the optical axis.

Some embodiments of a device comprise a light-guiding component, an optical-focusing component, and an optical-correction component. The optical-correction component is not directly attached to the optical-focusing component. Also, the optical-correction component has an optical power on a first axis, the optical-correction component has an optical power on a second axis, and the optical power on the first axis is different from the optical power on the second axis.

Some embodiments of a device comprise a light-guiding component, an optical-focusing component, a protector that surrounds at least part of the optical-focusing component and that includes a window, and an optical-correction component that is positioned in the window of the protector.

BRIEF DESCRIPTION OF THE DRAWINGS

FIGS. 7A-D illustrate sagittal views and tangential views of example embodiments of an optical probe and a sheath.

DETAILED DESCRIPTION

The following paragraphs describe certain explanatory embodiments. Other embodiments may include alternatives, equivalents, and modifications. Additionally, the explanatory embodiments may include several novel features, and a particular feature may not be essential to some embodiments of the devices, systems, and methods that are described herein.

Some optical-imaging devices (e.g., endoscopes) are configured to capture images from inside a subject, such as a human patient. These optical-imaging devices may include an optical probe, and the optical probe may include both a lens and a mirror at a distal tip. The lens and the mirror focus a beam of light, collect the beam of light, and guide the beam of light. Also, one or more optical fibers in the optical probe can be used to navigate the optical probe to an object (e.g., organs, tissues), deliver light to the object, and detect light that is reflected by the object. Furthermore, an optical-imaging device may include a sheath that encloses the optical probe.

For example, an optical probe that is configured for optical coherence tomography (OCT) can capture depth-resolved images of the blood vessels in the surface of an object (e.g., organ). As a beam of light from the optical probe is rotated across the surface, the optical probe can obtain cross-sectional images of the blood vessels in the surface. In order to obtain three-dimensional data, the optical probe can be translated longitudinally during the rotation to obtain images from a helical-scanning pattern. This helical scanning may be performed by pulling the tip of the optical probe back towards a proximal end while the optical probe is being rotated or by pushing the tip of the optical probe towards a distal end while the optical probe is being rotated.

The sheath may be transparent or mostly transparent so that the beam of light can travel through the sheath. The sheath has an optical power, although the optical power of the sheath is not very strong when the medium inside and the medium outside the sheath are the same (e.g., the media inside and outside the sheath are both air, the media inside and outside the sheath are both the same contrast agent). However, if the media are different, then the sheath has a stronger optical power. For example, if the medium inside the sheath is air and the medium outside the sheath is a contrast agent, then the sheath has a negative optical power in the sagittal direction. Additionally, the smaller the diameter of the sheath, the stronger the optical power of the sheath, and the greater the astigmatism caused by the sheath.

Figure 1:
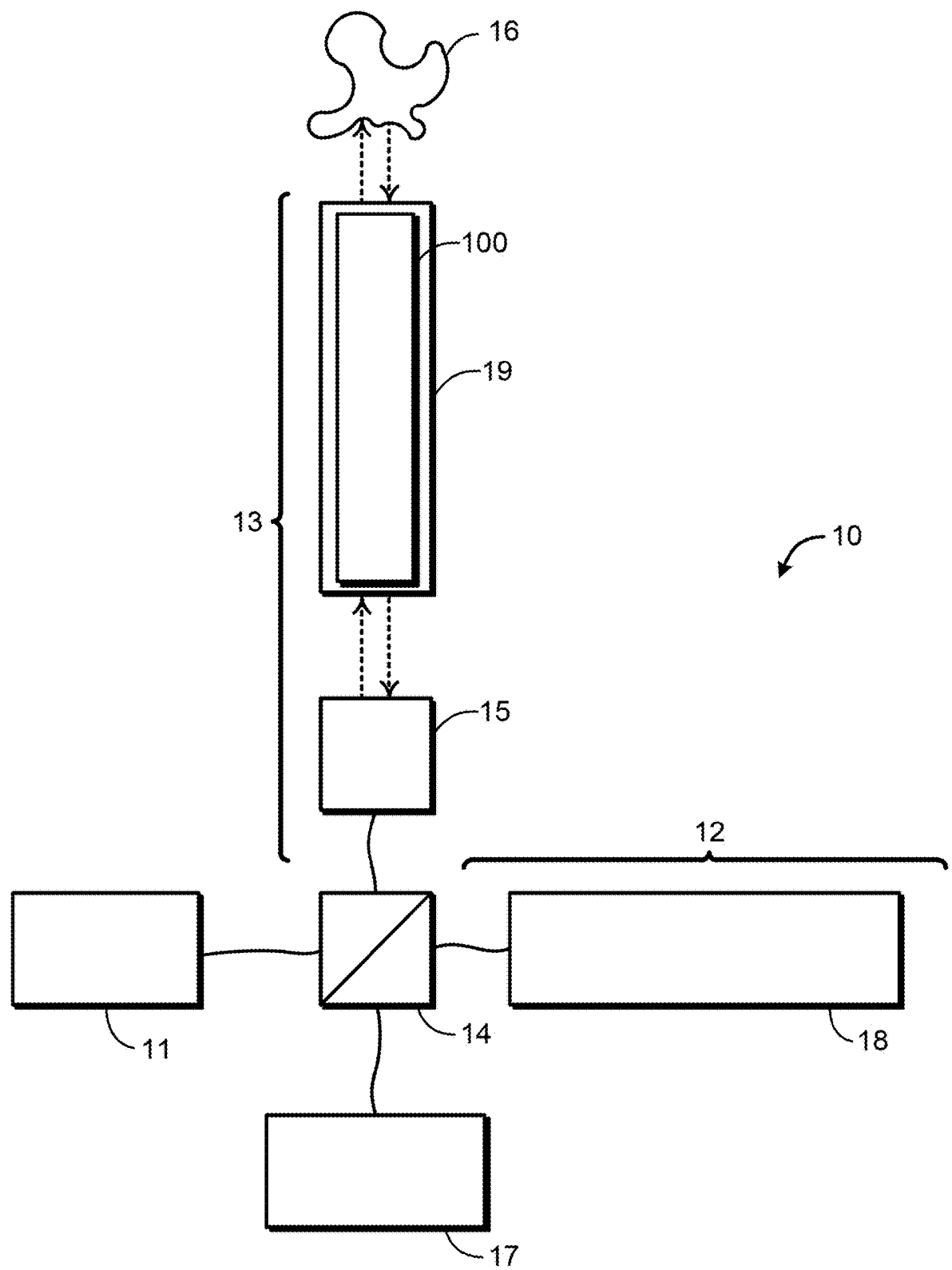
FIG. 1 illustrates an example embodiment of an optical-coherence-tomography (OCT) system.

FIG. 1 illustrates an example embodiment of an OCT system. The OCT system 10 includes a light source 11, a reference arm 12, a sample arm 13, a beam splitter 14, and one or more detectors 17. The light source 11 emits light, and the light source 11 may be, for example, a broad-band light source with a short coherence length, a superluminescent light-emitting diode (SLED), a tunable light source, a swept source laser, or a white-light source. The beam splitter 14 splits the light, directs some of the light to the reference arm 12, and directs some of the light to the sample arm 13.

Also, some embodiments of the OCT system 10 use one or more circulators to split the light and use one or more beam couplers to recombine the light.

The sample arm 13 includes a patient-interface unit 15 and an optical-imaging device 19. The optical-imaging device 19 includes an optical probe 100, which directs a beam of light to a sample 16 and detects light that is reflected from or scattered by the sample 16. The optical probe 100 then transmits this detected light back to the beam splitter 14.

The reference arm 12 includes an optical delay line 18. The optical delay line 18 includes a mirror, and light that travels through the optical delay line 18 is reflected off the mirror and then travels back to the beam splitter 14.

The beams from the sample arm 13 and the reference arm 12 are recombined by the beam splitter 14, which generates a recombined beam that has an interference pattern. The recombined beam is detected by the one or more detectors 17 (e.g., photodiodes, photomultiplier tubes, a linear CCD array, an image sensor, a CCD array, a CMOS array).

Figure 2:
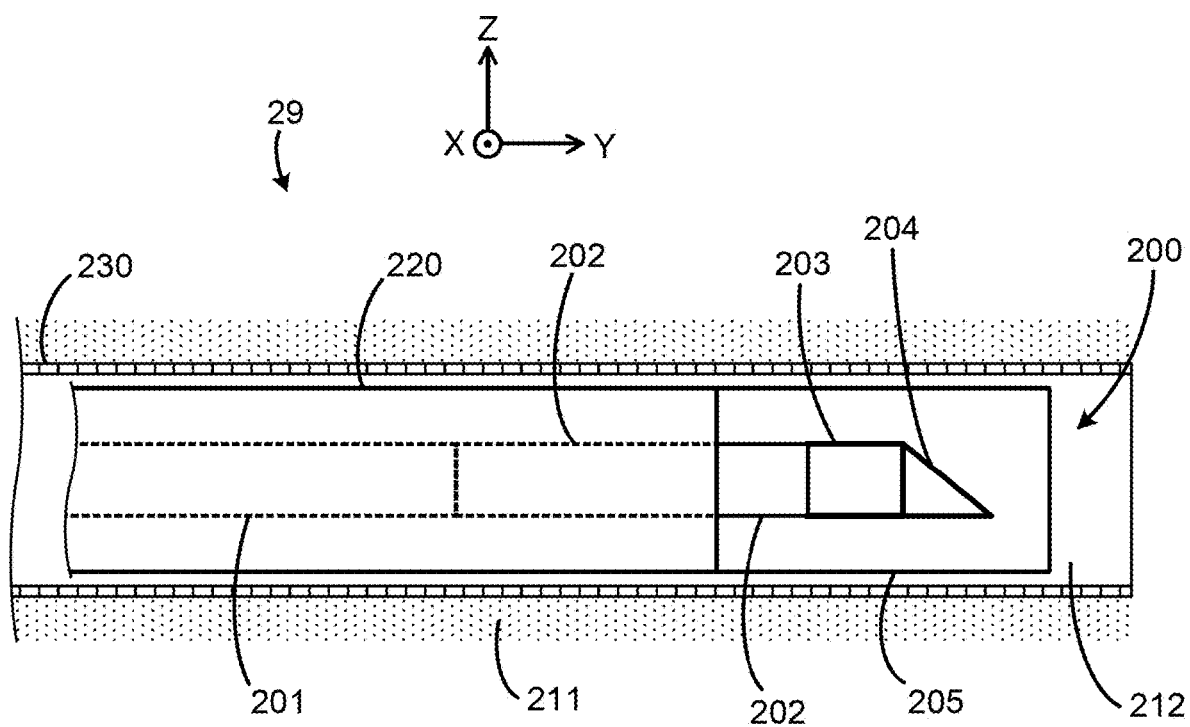
FIG. 2 illustrates a partially-cutaway view of an example embodiment of an optical-imaging device that includes an optical probe, a drive cable, and a sheath.

FIG. 2 illustrates a partially-cutaway view of an example embodiment of an optical-imaging device 29 (e.g., an optical-imaging catheter, an endoscope) that includes an optical probe 200, a drive cable 220, a protector 204, and a sheath 230. The optical probe 200 includes a first light-guiding component 201, which is a waveguide (e.g., a single-mode optical fiber, a multimode optical fiber, a double-clad optical fiber); a second light-guiding component 202, which is also a waveguide (e.g., a glass rod, a glass spacer, a large-core multimode fiber); an optical-focusing component 203 (e.g., a gradient-index (GRIN) lens, a ball lens, a half-ball lens, a graded-index (GI) fiber); and a light-reflecting component 204 (e.g., a prism). Also, the sheath 230 contains the protector 204, which surrounds part of the optical probe 200, and contains an inner medium 212 (e.g., air, a contrast agent), which is the medium inside the sheath 230. And the sheath 230 is surrounded by an outer medium 211 (e.g., air, a contrast agent), which is the medium outside the sheath 230. The sheath 230 may be mostly transparent or include a mostly-transparent window, and the sheath 230 may introduce a negative optical power along a first axis (e.g., the x axis in FIG. 2) and introduce almost no optical power along a second axis (e.g., the y axis in FIG. 2).

The drive cable 220, the protector 204, and the optical probe 200 are fixed relative to each other, and the optical probe 200 can freely spin inside of the sheath 230. The drive cable 220 delivers torque from its proximal end to its distal end in order to spin the distal end, which is attached to the optical probe 200. Spinning the optical probe 200 permits the optical probe to capture a 360° view.

Without correction, the optical-imaging system 29 may suffer from astigmatism caused by the sheath 230. The sheath's inner and outer surfaces are mostly flat in the tangential direction and thus have almost no influence on the optical power of the optical-imaging device 29. The sheath's inner and outer surfaces are curved in the sagittal direction. The inner surface has a negative optical power when air is the inner medium 212 because light travels from the air to the concave inner surface of the sheath 230. The outer surface has a positive optical power when air is the outer medium 211 because light travels from the concave outer surface of the sheath 230 to the air. However, the optical power at the outer surface is not as strong as the optical power at the inner surface because the radius of the curvature of the outer surface is larger than the radius of the curvature of the inner surface. Also, the sheath's material typically has an index of refraction (IOR) in the rage of 1.3 to 1.6, which causes the optical power of the outer sheath to be weaker or slightly negative when the outer medium 211 is a contrast agent and not air. Some contrast agents have an IOR in the range of 1.43 to 1.47.

Figure 3:
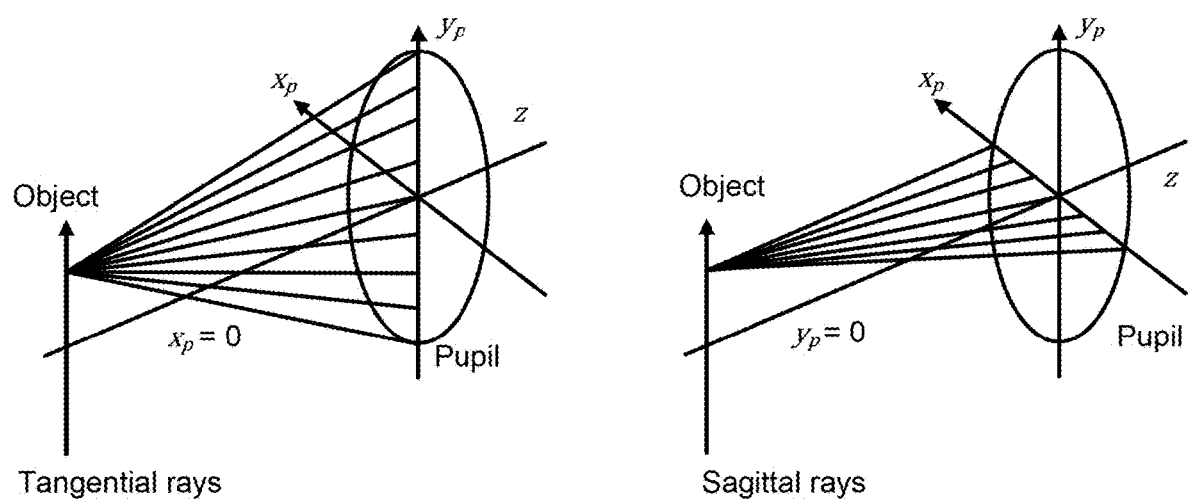
FIG. 3 illustrates ray definitions and a coordinate system.

FIG. 3 illustrates ray definitions and a coordinate system. Two sets of rays are used for aberration analysis: Tangential rays intersect the pupil at $x_p=0$, while sagittal rays intersect the pupil at $y_p=0$. The following description uses these ray definitions and this coordinate system.

Figure 4:
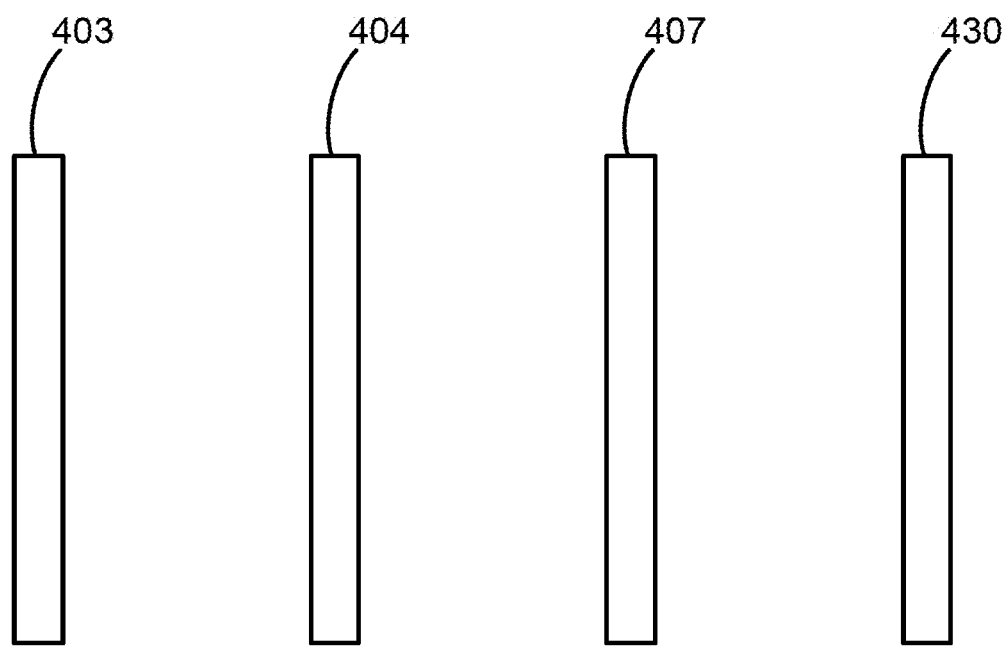
FIG. 4 is a generalized illustration of an example embodiment of an optical-imaging system.

FIG. 4 is a generalized illustration of an example embodiment of an optical-imaging system. The optical-imaging system includes an optical-focusing component 403 (e.g., a lens), a light-reflecting component 404, an optical-correction component 407, and a sheath 430.

In order to reduce or eliminate astigmatism, this embodiment of an optical-imaging system includes an independent optical-correction component 407 that is not directly attached to the primary optical component 403. In the optical path, the optical-correction component 407 is located between the optical-focusing component 403 and the sheath 430. The optical-correction component 407 may improve the optical performance of the system by enhancing the system's aperture, by correcting astigmatism, or both. The optical-correction component 407 can also increase an optical probe's aperture and lengthen the optical probe's working distance.

The optical-correction component 407 can correct astigmatism by means of at least one surface that has a curvature with an optical power. In some embodiments, the optical-correction component 407 acts as a lens that has a more-positive effective optical power in the sagittal direction than in the tangential direction, which can compensate for the sheath's negative optical power in the sagittal direction. And some embodiments have an optical-correction component 407 that acts as a lens that has a more-negative effective optical power in the tangential direction, which may compensate for the sheath's negative optical power in the sagittal direction.

Figure 5A:
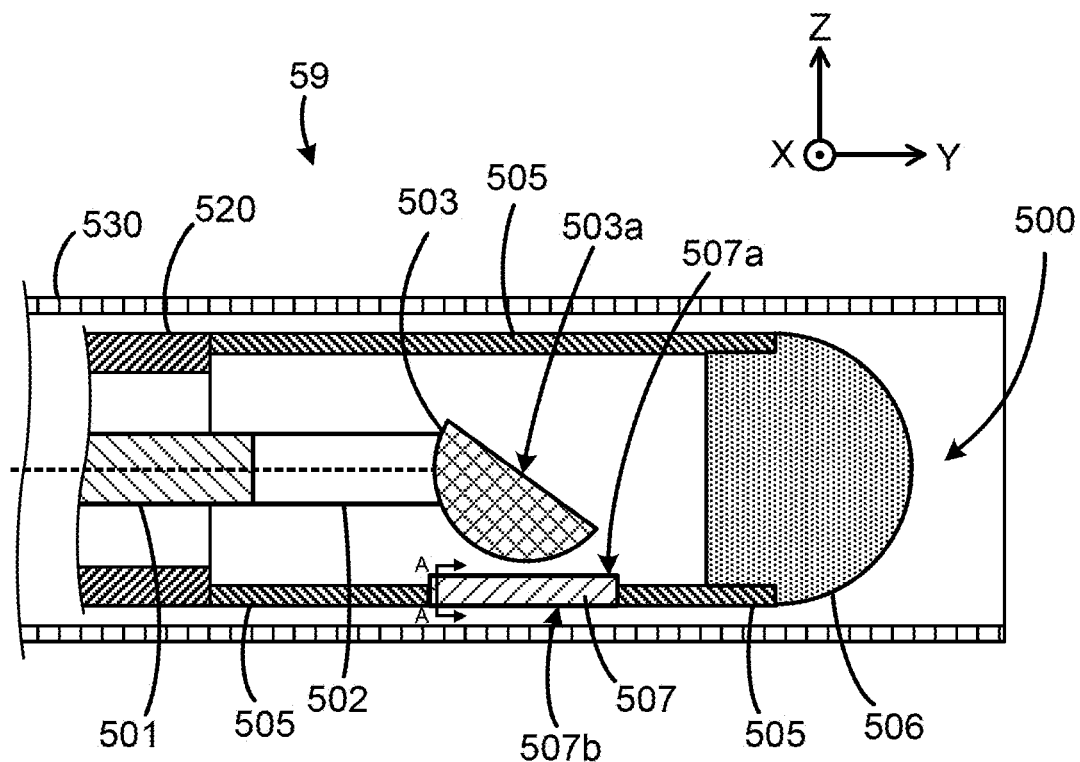
FIG. 5A illustrates a partially-cutaway view of an example embodiment of an optical-imaging device that includes an optical probe, a drive cable, and a sheath.

FIG. 5A illustrates a partially-cutaway view of an example embodiment of an optical-imaging device 59 that includes an optical probe 500, a drive cable 520, and a sheath 530. The optical probe 500 includes the following: a first light-guiding component 501 (e.g., an optical fiber); a second light-guiding component 502 (e.g., a glass-rod spacer); an optical-focusing component 503 (e.g., lens), which is also a beam-steering component in this embodiment; a protector 505; an atraumatic tip 506; and an optical-correction component 507.

The first light-guiding component 501 and the second light-guiding component 502 are configured to deliver one or more beams of light to the distal tip of the optical probe 500. The first light-guiding component 501 may be, for example, a double-clad fiber, a multimode fiber, a polarization-maintaining fiber, or a single-mode fiber. The second light-guiding component 502 may be, for example, a glass rod, a large-core fiber, or another spacer that can be used to adjust the numerical aperture (NA) of a beam of light to the entrance of the optical-focusing component 503. By using glass-rod spacers of different lengths, the numerical aperture (NA) may be adjusted. Also, in some embodiments, the optical properties of the glass-rod spacer are adjustable, thereby allowing the NA to also be adjusted. And in some embodiments, an end face of the second light-guiding component 502 is fusion spliced to an end face of the first light-guiding component 501.

Additionally, the y axis in FIG. 5A is aligned with a longitudinal axis of the first light-guiding component 501 or of the second light-guiding component 502. However, in some descriptions, the orientations of the x, y, and z axes are determined by the right-hand rule, in which the z axis is the axis of light propagation. Thus, if the z axis was the axis of light propagation, then the z axis in FIG. 5A would be aligned with the longitudinal axis of the first light-guiding component 501 or of the second light-guiding component 502.

In this embodiment, the optical-focusing component 503 is a ball lens that focuses a beam of light equally or nearly equally along orthogonal axes. Thus, the optical power of the ball lens may be equal or nearly equal on a first axis and on a second axis. Also, the ball lens may be attached to the second light-guiding component 502 or may be formed from an endface of the second light-guiding component 502, for example through a heating process. This embodiment of the optical-focusing component 503 includes a reflective surface 503a, which is a surface (e.g., a total-internal-reflection (TIR) surface) that has a mirror finish or a surface that does not meet the TIR conditions and has a deposited layer that acts as a mirror. The deposited layer could be, for example, protected silver, gold, or aluminum. Additionally, this embodiment of the reflective surface 503a has a negligible optical power or does not have an optical power.

Because of its cylindrical shape, the sheath 530 has an asymmetric optical power that refracts light from the optical probe 500. For example, the clear or mostly-clear sheath 530 (or window of the sheath 530) may introduce a negative optical power along a first axis (e.g., the x axis in FIG. 3A) and may introduce almost no optical power along a second axis (e.g., the y axis in FIG. 3A).

In this embodiment, the optical-correction component 507 is an approximately-cylindrical lens. The lens has a refractive surface that introduces almost no optical power in both the sagittal and the tangential directions and has a refractive surface that introduces a positive optical power in the sagittal direction and almost no optical power in the tangential direction. Thus, the optical-correction component 507 compensates for the optical power of the sheath 530.

Also, the components of the optical-imaging device 59 can be selected to suit a particular environment. Some embodiments of the optical-imaging device 59 are specially configured for use in an air environment, and some embodiments of the optical-imaging device 59 are specially configured for use in a liquid environment. The liquids that compose the liquid environment may include, for example, saline, dextran, water, or a combination of liquids. The optical-focusing component 503, the optical-correction component 507, and the sheath 530 may be selected according to the refractive index of the environment in which the optical-imaging device 59 will be used.

For example, in some embodiments, the optical-focusing component 503 can be described by $P_x=P_y=P_{Desired}$ (where $P_x$ is the power on the x axis, $P_y$ is the power on the y axis, and $P_{Desired}$ is the desired total power of the optical-imaging device 59), the optical-correction component 507 can be described by $P_x$=Positive Optical Power and $P_y$=0, and the sheath 530 can be described by $P_x$=Negative Optical Power and $P_y$=0. Note that this notation assumes that the z axis is the axis of light propagation both before and after the reflection from the optical-focusing component 503, which eliminates the need to describe the axis change in FIG. 5A that is caused by the reflection of the optical-focusing component 503.

Figure 5B:
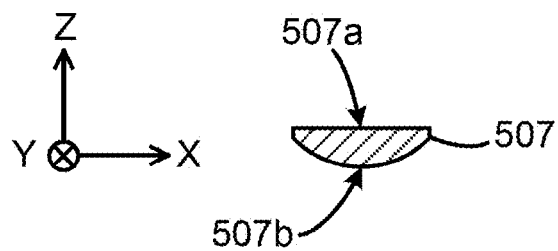
FIG. 5B shows an example embodiment of the optical-correction component in FIG. 5A from the viewpoint of line A-A.

Additionally, in some embodiments, a first surface 507a of the optical-correction component 507 is mostly planar and has no optical power, and a second surface 507b of the optical-correction component 507 is a cylindrical concave surface that introduces a positive optical power on a first axis (e.g., the x axis in FIG. 5A). The positive optical power on the first axis may match the effect of the sheath's negative optical power on the first axis. FIG. 5B shows an example embodiment of the optical-correction component 507 in FIG. 5A from the viewpoint of line A-A.

In some embodiments, the optical-correction component 507 has an optical power on both surfaces. Also, the surfaces of the optical-correction component 507 can be anamorphic, and thus have an optical power on a first axis that is different from an optical power on a second axis.

Furthermore, in some embodiments, the reflective surface 503a of the optical-focusing component 503 has an optical power on one or two axes. In these embodiments, the optical-correction component 507 may not be necessary. Additionally, the optical-focusing component 503 can be composed of a GRIN lens and a polished prism. And some embodiments of the optical probe 500 do not include the optical-focusing component 503 and instead include a second light-guiding component 502 that has been polished to steer the beam.

Moreover, some embodiments of the optical probe 500 are configured to transmit and emit beams of light in more than one wavelength. For example, some embodiments that are configured for multimodal optical coherence tomography emit one beam that has a wavelength that is suitable for OCT and emit another beam that has a wavelength that is suitable for fluorescence imaging. The sizes of the members of the optical probe 500 and the arrangement of the members of the optical probe 500 may be configured to produce a desired beam width and a desired working distance.

Some embodiments of the optical probe 500 are configured for a multimodality system that simultaneously performs OCT imaging using light with a wavelength of 1.31 µm and fluorescence mapping using light with a wavelength of 0.633 µm. Depending on the specification of the imaging, it may be critical to focus the OCT wavelength, which can provide structural information, at a designed optimal working distance to provide lateral resolution, while the fluorescence wavelength is focused slightly off from the optimal working distance of the OCT imaging, thereby allowing the fluorescence wavelength to have a larger beam size with a lower lateral resolution at the optimal working distance of the OCT imaging.

For example, in coronary arteries, the diameters of the arteries of interest are often about 2 to 4 mm. Assuming that the optical probe 500 is located at the center of the artery, the radius of the artery corresponds to the working distance, and is 1 to 2 mm from the optical axis of the optical probe 500.

OCT and fluorescence wavelengths both penetrate the vessel, so, in some embodiments, the focus position or the working distance is optimal at 1 to 3 mm. Within these working distances, the focus may be different between the two modalities. Some embodiments of the optical probe 500 (e.g., for coronary-artery measurement) have focal distances or working distances that are within 2 mm of each other, for example the embodiment in FIG. 8. Some embodiments have larger differences in the focal distances or working distances, for example embodiments that are used for larger blood vessels (e.g., peripheral arteries), corresponding to the blood vessel's diameter and the desired working distance.

The optimization of the focal point may be accomplished by using the refractive indices for the two wavelengths and solving the optimization problem. When optimizing, it may be efficient to add another material, with a different combination of refractive indices for the two wavelengths, by splitting one or more optical components or by adding a spacer.

Also, some embodiments of the optical probe 500 are configured for other modalities, such as near-infrared spectroscopy, in addition to or in alternative to OCT and fluorescence imaging.

Figure 6A:
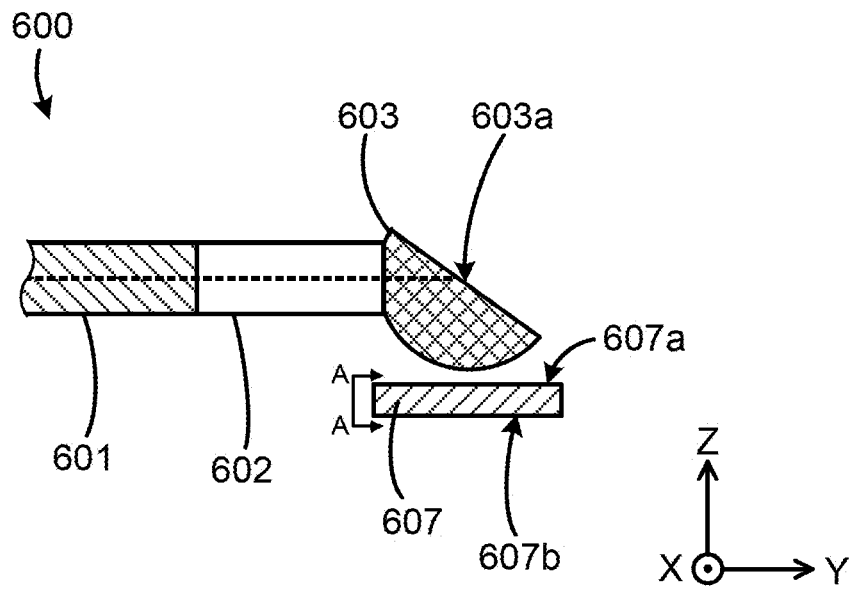
FIG. 6A illustrates an example embodiment of an optical probe.

FIG. 6A illustrates an example embodiment of an optical probe. The optical probe 600 includes the following: a first light-guiding component 601 (e.g., an optical fiber); a second light-guiding component 602 (e.g., a glass-rod spacer); an optical-focusing component 603 (e.g., lens), which is also a beam-steering component in this embodiment; and an optical-correction component 607.

Figure 6B:
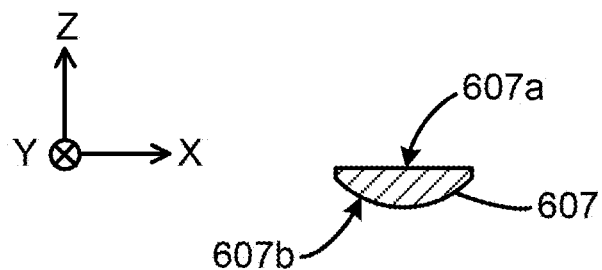
FIG. 6B shows an example embodiment of the optical-correction component in FIG. 6A from the viewpoint of line A-A.

The optical-correction component 607 includes a first refractive surface 607a. In this embodiment, the first refractive surface 607a is mostly planar, has no optical power on a first axis (e.g., the x axis in FIG. 6A), and has no optical power on a second axis (e.g., the y axis in FIG. 6A). The optical-correction component 607 also includes a second refractive surface 607b. In this embodiment, the second refractive surface 607b is a convex or a mostly-convex surface that has a positive optical power along the first axis (e.g., the x axis in FIG. 6A) and that has little or no optical power along the second axis (e.g., the y axis in FIG. 6A). FIG. 6B shows an example embodiment of the optical-correction component 607 in FIG. 6A from the viewpoint of line A-A.

FIGS. 7A-D illustrate sagittal views and tangential views of example embodiments of an optical probe and a sheath. FIGS. 7A-B show a tangential view and a sagittal view of an embodiment of an optical probe 700a that includes a first light-guiding component 701, a second light-guiding component 702, and an optical-focusing component 703, but does not include an optical-correction component 707. FIGS. 7C-D show a tangential view and a sagittal view of an embodiment of an optical probe 700b that includes a first light-guiding component 701, a second light-guiding component 702, an optical-focusing component 703, and an optical-correction component 707.

In FIGS. 7A-D, light that was transmitted by the first light-guiding component 701, which is a double-clad fiber that has a numerical aperture of 0.09, travels through the second light-guiding component 702, which is a coreless fiber that is 240 µm long. The light then enters the optical-focusing component 703, which is a fused-silica ball lens that has a diameter of 300 µm. The optical-focusing component 703 is angle polished such that the incident angle of the light to the polished surface is about 51°. The light is reflected by the polished surface and then travels through the bottom curvature of the optical-focusing component 703 toward the sheath 730.

The sheath 730 has an inner diameter of 0.584 mm, an outer diameter of 0.787 mm, and a refractive index of about 1.5. The chief-ray incident angle to the sheath 730 in the tangential direction is about 20° in air. And the sheath 730 is immersed in a contrast agent 711, which has a refractive index of 1.45.

In the embodiment that is shown in FIGS. 7A-B, the light leaves the bottom curvature of the optical-focusing component 703, travels through air, and then travels through the sheath 730. Because of the negative optical power of the sheath 730, the light diverges in the sagittal direction.

In contrast, in the embodiment that is shown in FIGS. 7C-D, the light leaves the bottom curvature of the optical-focusing component 703, travels through air, and then travels through the optical-correction component 707 before traveling through more air and then the sheath 730. In this embodiment, the optical-correction component 707 is a Plano-convex lens that is made of BK7. The optical-correction component 707 is 100 µm thick, and its radius of curvature is 280 µm on its curved surface. There is a 20 µm air gap between the optical-correction component 707 and the optical-focusing component 703, and there is a 20 µm air gap between the optical-correction component 707 and the inner surface of the sheath 730. The astigmatisms of an OCT beam at the wavelength of 1310 µm and of a fluorescent beam at wavelength of 633 µm are both corrected such that the beams focus at a point that is 1.7 mm away, measured vertically, from the longitudinal axis of the optical probe 700b. For example, if the sheath 730 had an outer radius of 0.4 mm, and if the focus point was 1.7 mm from the longitudinal axis of the sheath 730, then the focus point would be 1.3 mm from the outer diameter of the sheath 730.

Figure 8:
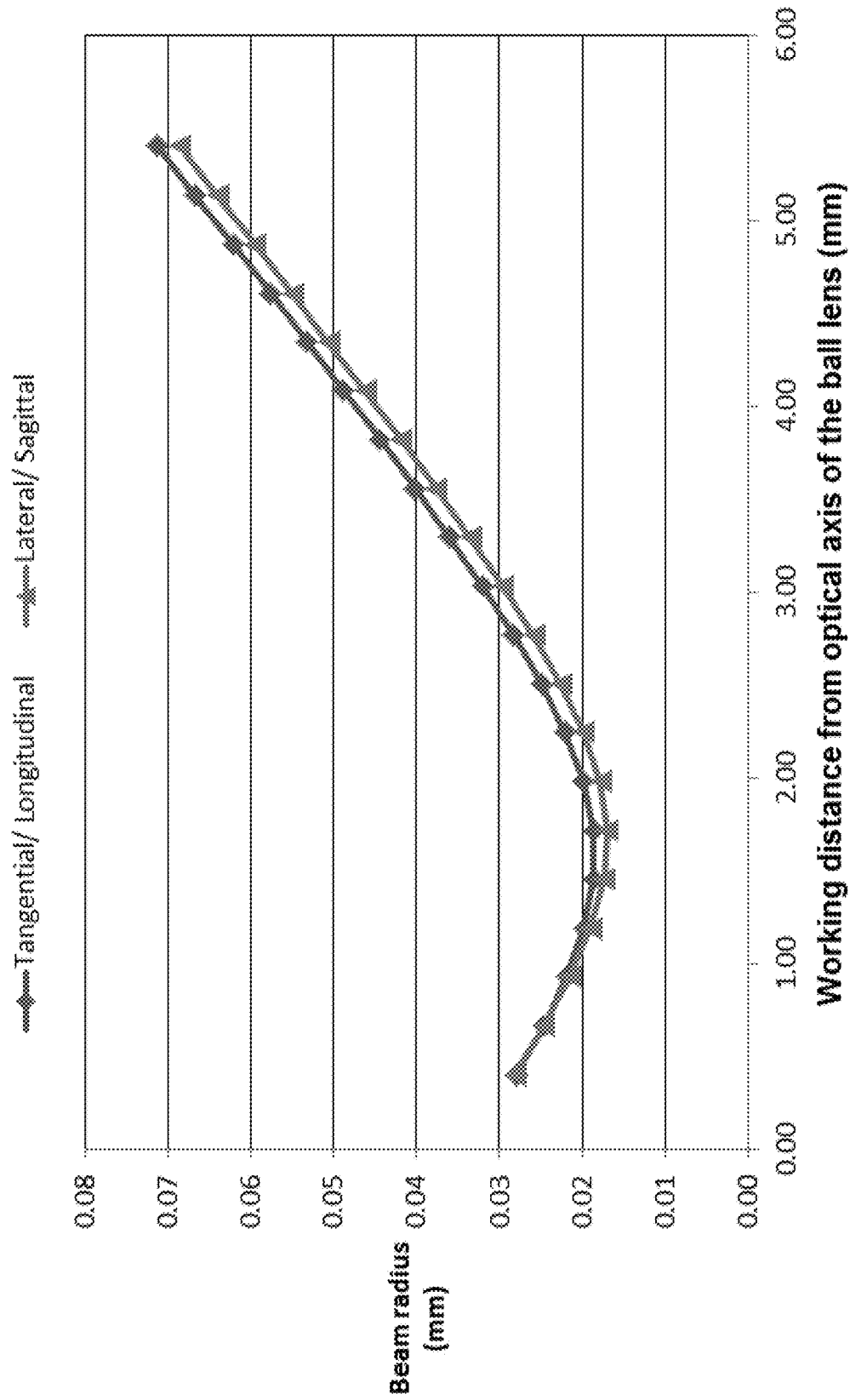
FIG. 8 shows a plot of the beam radius versus working distance for the example embodiment of an optical probe and a sheath that is shown in FIGS. 7C-D.

FIG. 8 shows a plot of the beam radius versus working distance for the example embodiment of the optical probe 700b and the sheath 730 that is shown in FIGS. 7C-D. FIG. 8 shows that that the beam of light in the λ=1.31 µm wavelength focuses at the same distance (~1.7 mm from the optical axis of the optical probe) in both the tangential and the sagittal directions.

Figure 9:
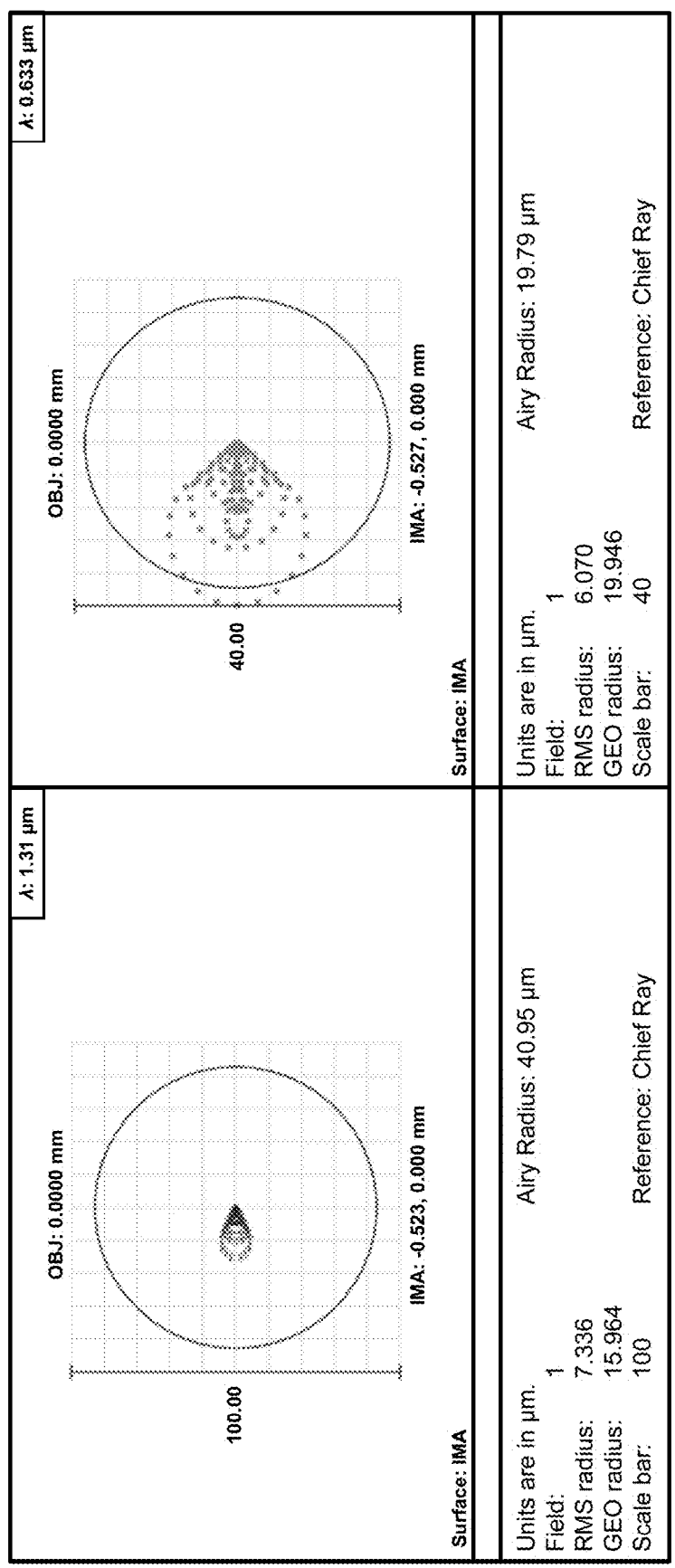
FIG. 9 illustrates the geometrical spot radii in the $\lambda=1.31$ µm and the $\lambda=0.633$ µm wavelengths at a focus point that is 1.7 mm away, vertically, from an optical axis of the optical probe in the example embodiment of an optical probe and a sheath that is illustrated in FIGS. 7C-D.

FIG. 9 illustrates the geometrical spot radii in the λ=1.31 µm and the λ=0.633 µm wavelengths at a focus point that is 1.7 mm away, measured vertically, from the optical axis of the optical probe 700b in the example embodiment of the optical probe 700b and the sheath 730 that is illustrated in FIGS. 7C-D. The diffraction limit has a 40.95 µm Airy radius in the wavelength λ of 1.31 µm (λ=1.31 µm) and has a 19.79 µm Airy radius in the wavelength λ of 0.633 µm (λ=0.633 µm).

Figures 10A, 10B, 10C, 10D:
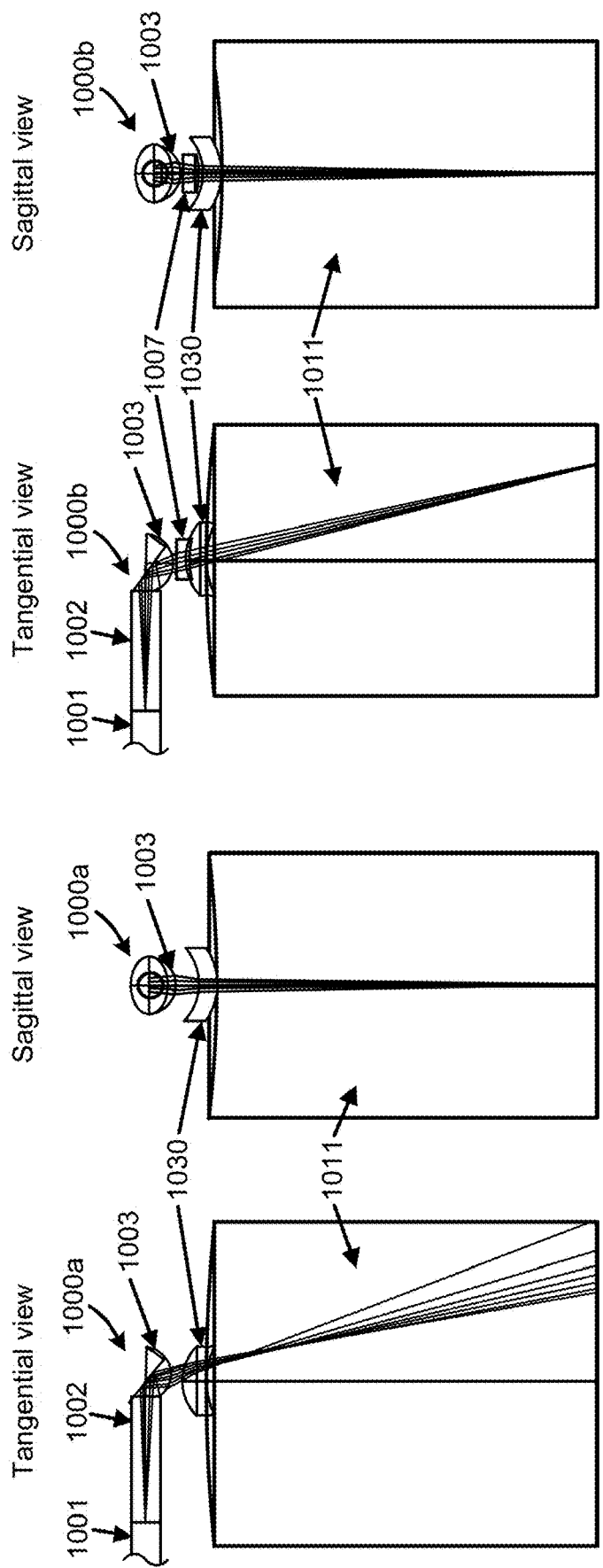
FIGS. 10A-D illustrate sagittal views and tangential views of example embodiments of an optical probe and a sheath.

FIGS. 10A-D illustrate sagittal views and tangential views of example embodiments of an optical probe and a sheath. FIGS. 10A-B show a tangential view and a sagittal view of an embodiment of an optical probe 1000a that includes a first light-guiding component 1001, a second light-guiding component 1002, and an optical-focusing component 1003, but does not include an optical-correction component. FIGS. 10C-D show a tangential view and a sagittal view of an embodiment of an optical probe 1000b that includes a first light-guiding component 1001, a second light-guiding component 1002, an optical-focusing component 1003, and an optical-correction component 1007.

In FIGS. 10A-D, light that was transmitted by the first light-guiding component 1001, which is a double-clad fiber that has a numerical aperture of 0.09, travels through the second light-guiding component 1002, which is a coreless fiber that is 660 µm long. The light then enters the optical-focusing component 1003, which is a fused-silica ball lens that has a diameter of 300 µm. The optical-focusing component 1003 is angle polished such that the incident angle of the light to the polished surface is about 51°. The light is reflected by the polished surface and then travels through the bottom curvature of the optical-focusing component 1003 toward the sheath 1030.

The sheath 1030 has an inner diameter of 0.584 mm, an outer diameter of 0.787 mm, and a refractive index of about 1.5. The chief-ray incident angle to the sheath 1030 in the tangential direction is about 20° in air. And the sheath 1030 is immersed in a contrast agent 1011, which has a refractive index of 1.45.

In the embodiment that is shown in FIGS. 10A-B, the light leaves the bottom curvature of the optical-focusing component 1003, travels through air, and then travels through the sheath 1030. Because of the negative optical power of the sheath 1030, the light diverges in the tangential direction.

In contrast, in the embodiment that is shown in FIGS. 10C-D, the light leaves the bottom curvature of the optical-focusing component 1003, travels through air, and then travels through an optical-correction component 1007 before traveling through air again and then through the sheath 1030. In this embodiment, the optical-correction component 1007 is a Plano-convex lens that is made of BK7. The optical-correction component 1007 is 80 µm thick, and its radius of curvature is 450 µm on its curved surface. There is a 20 µm air gap between the optical-correction component 1007 and the optical-focusing component 1003, and there is a 42 µm air gap between the center of the optical-correction component 1007 and the inner surface of the sheath 1030. The astigmatisms of an OCT beam at the wavelength of 1310 µm and of a fluorescent beam at wavelength of 633 µm are both corrected such that the beams focus at a point that is 1 mm away, measured vertically, from the longitudinal axis of the optical probe 1000b.

The scope of the claims is not limited to the above-described embodiments and includes various modifications and equivalent arrangements. Also, as used herein, the conjunction "or" generally refers to an inclusive "or," although "or" may refer to an exclusive "or" if expressly indicated or if the context indicates that the "or" must be an exclusive "or."

The invention claimed is:

1. A device comprising:
   a sheath;
   a first light-guiding component;
   a second light-guiding component;
   an optical-focusing component, wherein the second light-guiding component and the optical-focusing component are aligned on an optical axis;
   an optical-correction component, wherein the optical-correction component does not directly contact the optical-focusing component, wherein the optical-correction component is not positioned on the optical axis, and wherein the optical-correction component has a first planar or mostly planar surface and at least one additional surface having a curvature with an optical power; and
   a protector that surrounds at least a part of the optical-focusing component and at least a part of the second light-guiding component, the protector including a window, wherein the optical-correction component is mounted in the window such that (i) the first planar or mostly planar surface is positioned towards an inside of the protector and extends from at least one side of the window to at least an opposite side of the window, and (ii) the at least one additional surface is aligned with an exterior surface of the protector.

2. The device of claim 1, wherein the optical-focusing component is configured to one or more of the following: (i) act as a beam-steering component that directs light received from the second light-guiding component toward the optical-correction component; and/or (ii) substantially determine an angle of the light as the light crosses a window optical component of the sheath and exits a catheter or probe of the device.

3. The device of claim 1, wherein the optical-focusing component is one of a gradient-index lens, a GI-fiber lens, a ball lens, a ball lens that is angled polished, a ball lens that is less than a full ball lens, an optical-focusing component that is angle polished, and a half-ball lens.

4. The device of claim 1, wherein the optical-correction component operates to one or more of the following: (i) correct, reduce, or eliminate astigmatism; (ii) improve an optical performance of the device by enhancing or increasing an aperture of the device; (iii) lengthen a working distance of an optical probe or probe of the device; and/or (iv) compensate for an optical power of the sheath.

5. The device of claim 4, wherein one or more of the following:
   (i) the optical-correction component operates to correct, reduce, or eliminate the astigmatism via the at least one additional surface that has the curvature with the optical power; and/or
   (ii) the at least one additional surface of the optical-correction component is convex or concave along an axis that is lateral, perpendicular, or transverse to the optical axis.

6. The device of claim 5, wherein the optical-correction component operates to correct, reduce, or eliminate the astigmatism by acting as a lens that has a more-positive effective optical power in a sagittal direction than in a tangential direction such that the optical-correction component operates to compensate for a negative optical power in the sagittal direction of the sheath.

7. The device of claim 1, wherein the optical-focusing component has an optical power on a first axis and an optical power on a second axis that is orthogonal to the first axis, and wherein the optical power on the first axis is equal to the optical power on the second axis.

8. The device of claim 7, wherein the sheath has a negative optical power on the first axis.

9. The device of claim 8, wherein one or more of the following: (i) the optical-correction component has a positive optical power on the first axis, and/or (ii) the optical-correction component has an optical power of zero on the second axis.

10. The device of claim 1, wherein the sheath includes a catheter or probe window as an additional optical component, and the device operates to reduce or eliminate an astigmatism caused by a shape of the sheath.

* * * * *